US012616596B2

(12) United States Patent
Rehbein et al.

(10) Patent No.: US 12,616,596 B2
(45) Date of Patent: May 5, 2026

(54) NEGATIVE PRESSURE THERAPY SYSTEM WITH IMMOBILIZING LOCKING SHEETS

(71) Applicant: KCI Manufacturing Unlimited Company, Westmeath (IE)

(72) Inventors: Jonathan G. Rehbein, San Antonio, TX (US); Christopher Carroll, San Antonio, TX (US); Thomas Corrigan, San Antonio, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 319 days.

(21) Appl. No.: 18/277,815

(22) PCT Filed: Feb. 21, 2022

(86) PCT No.: PCT/IB2022/051522
§ 371 (c)(1),
(2) Date: Aug. 18, 2023

(87) PCT Pub. No.: WO2022/195378
PCT Pub. Date: Sep. 22, 2022

(65) Prior Publication Data
US 2024/0307210 A1 Sep. 19, 2024

Related U.S. Application Data

(60) Provisional application No. 63/162,192, filed on Mar. 17, 2021.

(51) Int. Cl.
*A61F 5/00* (2006.01)
*A61F 5/058* (2006.01)
(52) U.S. Cl.
CPC ........ *A61F 5/05833* (2013.01); *A61F 5/0585* (2013.01)

(58) Field of Classification Search
CPC ........... A61B 2017/00566; A61B 2017/00955; A61B 2017/00858; A61B 2017/00862
See application file for complete search history.

(56) References Cited

U.S. PATENT DOCUMENTS

| | | | |
|---|---|---|---|
| 1,355,846 A | 10/1920 | Rannells | |
| 2,547,758 A | 4/1951 | Keeling | |
| (Continued) | | | |

FOREIGN PATENT DOCUMENTS

| | | | |
|---|---|---|---|
| AU | 550575 B2 | 3/1986 | |
| AU | 745271 B2 | 3/2002 | |
| (Continued) | | | |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Kim M Lewis

(57) ABSTRACT

An injury treatment system includes a negative pressure source and a dressing pneumatically communicable with the negative pressure source. The dressing includes a negative pressure therapy component configured to expose an anatomical structure to a negative pressure when the negative pressure therapy component is applied to the anatomical structure and in response to operation of the negative pressure source. The dressing also includes an immobilization component coupled to the negative pressure therapy system, wherein the immobilization component is configured to transition from a flexible state to an inflexible state in response to the operation of the negative pressure source.

14 Claims, 8 Drawing Sheets

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,978,885 A * | 9/1976 | Lu .......................... F16K 15/00 |
| | | 251/319 |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 10,538,049 B2 * | 1/2020 | Corrigan ................ B65D 65/38 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2012/0310126 A1 * | 12/2012 | Bureau ............... A61F 5/05833 |
| | | 602/6 |
| 2014/0163491 A1 | 6/2014 | Schuessler et al. |
| 2015/0080788 A1 | 3/2015 | Blott et al. |
| 2015/0369325 A1 | 12/2015 | Bureau et al. |
| 2016/0354253 A1 * | 12/2016 | Hunt ..................... A61M 27/00 |
| 2020/0085992 A1 | 3/2020 | Locke et al. |
| 2020/0253788 A1 | 8/2020 | Rehbein et al. |

FOREIGN PATENT DOCUMENTS

| | | | | |
|---|---|---|---|---|
| AU | 755496 | B2 | 12/2002 | |
| CA | 2005436 | A1 | 6/1990 | |
| CA | 2905655 | A1 * | 8/2014 | ............... F16F 9/04 |
| DE | 2640413 | A1 | 3/1978 | |
| DE | 4306478 | A1 | 9/1994 | |
| DE | 29504378 | U1 | 9/1995 | |
| EP | 0100148 | A1 | 2/1984 | |
| EP | 117632 | A2 | 9/1984 | |
| EP | 161865 | A2 | 11/1985 | |
| EP | 358302 | A2 | 3/1990 | |
| EP | 1018967 | A1 | 7/2000 | |
| GB | 692578 | A | 6/1953 | |
| GB | 2195255 | A * | 4/1988 | ............ A61H 9/005 |
| GB | 2197789 | A | 6/1988 | |
| GB | 2220357 | A | 1/1990 | |
| GB | 2235877 | A | 3/1991 | |
| GB | 2329127 | A | 3/1999 | |
| GB | 2333965 | A | 8/1999 | |
| JP | 4129536 | B2 | 8/2008 | |
| SG | 71559 | | 4/2002 | |
| WO | 80/02182 | A1 | 10/1980 | |

(56) References Cited

FOREIGN PATENT DOCUMENTS

| WO | 8704626 | A1 | 8/1987 | | |
| WO | 90010424 | A1 | 9/1990 | | |
| WO | 93009727 | A1 | 5/1993 | | |
| WO | 94020041 | A1 | 9/1994 | | |
| WO | 9605873 | A1 | 2/1996 | | |
| WO | 9718007 | A1 | 5/1997 | | |
| WO | 9913793 | A1 | 3/1999 | | |
| WO | WO-0126560 | A1 * | 4/2001 | ............ | A61B 17/02 |
| WO | 2011079865 | A1 | 7/2011 | | |
| WO | 2013113332 | A1 | 8/2013 | | |
| WO | WO-2016100182 | A1 * | 6/2016 | ............... | A61F 5/01 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 p. English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.@ Therapy Clinical Guidelines: A Reference Source for Clinicians; Jul. 2007.
PCT International Search Report/Written Opinion for PCT/IB2022/051522, mailed Jun. 3, 2022.
Japanese Notice of Rejection for corresponding application 2023-555230, dated Jan. 20, 2026.

* cited by examiner

300

302

304

NEGATIVE PRESSURE THERAPY SYSTEM WITH IMMOBILIZING LOCKING SHEETS

CROSS-REFERENCE TO RELATED APPLICATIONS

This application claims the benefit of priority to U.S. Provisional Application No. 63/162,192, filed on Mar. 17, 2021, which is incorporated herein by reference in its entirety.

BACKGROUND

Swelling associated with trauma or certain pathologies (e.g. lymphedema) may cause various medical complications. For example, swelling can cause discomfort and pain, may limit range of motion, or otherwise negatively impact patient quality of life. Swelling may also limit the ability of a medical provider to medically image, view, access underlying tissue, or may otherwise interfere in the treatment of a patient, and thus may pose an impediment to the healing and recovery of the patient. In certain circumstances, swelling may lead to even more severe consequences, such as, e.g., atrophy of surrounding muscle tissue. It would be advantageous to provide a system which could help reduce swelling at a tissue site, for example by providing decompression therapy to increase blood perfusion and lymphatic flow at a tissue site to reduce swelling at the tissue site. In some clinical scenarios, immobilization of the tissue site (e.g., of a joint) may also be desirable in coordination with decompression therapy to improve patient outcomes. Coordinated or integrated treatment for both immobilization and swelling reduction may be challenging.

SUMMARY

One implementation of the present disclosure is an injury treatment system. The injury treatment system includes a negative pressure source and a dressing pneumatically communicable with the negative pressure source. The dressing includes a negative pressure therapy component configured to expose an anatomical structure to a negative pressure when the negative pressure therapy component is applied to the anatomical structure and in response to operation of the negative pressure source. The dressing also includes an immobilization component coupled to the negative pressure therapy system, wherein the immobilization component is configured to transition from a flexible state to an inflexible state in response to the operation of the negative pressure source.

In some embodiments, the negative pressure therapy component comprises a manifolding layer and an air-impermeable layer configured to be sealed to the anatomical structure to define an airtight volume containing the manifolding layer between the air-impermeable layer and the anatomical structure.

In some embodiments, the immobilization component is further configured to transition from the inflexible state to the flexible state in response to release of negative pressure from the immobilization component. The immobilization component may be pneumatically communicable with the negative pressure source via the negative pressure therapy component. In some embodiments, the immobilization component is pneumatically communicable with the negative pressure source via a valve configured to close when a threshold amount of negative pressure is established in the immobilization component.

In some embodiments, the anatomical structure includes joint of a patient and the immobilization component is configured to substantially immobilize the joint when in the inflexible state. The immobilization component may include an airtight chamber configured to be evacuated by the operation of the negative pressure source and locking sheets positioned in the airtight chamber. In such embodiments, the locking sheets are flexible when the airtight chamber is not evacuated and interlock to form a rigid structure when the airtight chamber is evacuated by the operation of the negative pressure source.

Another implementation of the present disclosure is an injury treatment device. The injury treatment device includes a manifold layer having a patient-facing side and a non-patient-facing side, a first airtight chamber positioned along at least a portion of the non-patient-facing side of the airtight chamber, and locking sheets positioned in the first airtight chamber. The locking sheets are configured to transition from a flexible state to an inflexible state. The injury treatment device also includes a sealable layer coupled to the manifold layer and configured to be sealed to a patient to define a second airtight chamber that contains the manifold layer.

In some embodiments, the injury treatment system includes a valve configured to selectively place the first airtight chamber in fluid communication with the second airtight chamber.

In some embodiments, the locking sheets are flexible when the first airtight chamber is at atmospheric pressure, and, when the first airtight chamber is drawn to at least a threshold negative pressure, the locking sheets are inflexible. The threshold negative pressure may be −125 mmHg.

In some embodiments, the locking sheets include a first sheet having protrusions arranged in a first pattern and a second sheet having recesses arranged in the first pattern. The first sheet is substantially prevented from sliding along the second sheet when the protrusions are positioned in the recesses, thereby rendering the locking sheets inflexible. The protrusions may be configured to enter the recesses in response to establishment of a negative pressure in the airtight chamber and move out of the recesses in response to release of the genitive pressure from the airtight chamber.

In some embodiments, the injury treatment device is configured for application to a patient's ankle. The manifold layer may have a first boot-like shape, and the locking sheets may be less-than-coextensive with the manifold layer. For example, the locking sheets may be provided in a splinting arrangement configured to substantially immobilize the ankle when the locking sheets are in the inflexible state and to allow the ankle to be inserted into the boot-like shape of the manifold layer when the locking sheets are in the flexible state.

Another implementation of the present disclosure is a method of treating an injury to a joint. The method includes applying a treatment device around the joint, sealing one or more edges of the treatment device to the joint to define a first airtight chamber containing a manifold layer, providing negative pressure therapy by pumping air out of the first airtight chamber to communicate a negative pressure to the joint, and providing immobilization therapy by pumping air out of a second airtight chamber. The second airtight chamber contains locking sheets configured to immobilize the joint in response to the second airtight chamber reaching at least a threshold negative pressure.

In some embodiments, pumping the air out of the first airtight chamber and the second airtight chamber is performed by operating a pump in fluid communication with both the first airtight chamber and the second airtight chamber. In some embodiments, pumping the air out of the second airtight chamber includes drawing the air from the second airtight chamber through the first airtight chamber. In some embodiments, providing the immobilization therapy includes closing a valve of the second airtight chamber when the second airtight chamber reaches the threshold negative pressure.

In some embodiments, the method also includes ending the treating of the injury by allowing air to flow into the second airtight chamber to cause the locking sheets are configured to transition from an inflexible state to a flexible state, unsealing the first airtight chamber, and removing the treatment device the joint. The method may also include cleaning the treatment device for reuse.

Another implementation of the present disclosure is an injury treatment system. The injury treatment system includes an airtight pouch, a negative pressure source pneumatically communicable with the airtight pouch and operable to establish a negative pressure in the airtight pouch, and a plurality of sheets positioned in the airtight pouch, wherein each sheet has a thickness in a range between approximately 0.004" and 0.006". The plurality of sheets are configured to jam together to form an inflexible block when the negative pressure source establishes the negative pressure in the airtight pouch.

In some embodiments, a combined thickness of the plurality of sheets is in a range between 0.125" and 0.25" inches. The plurality of sheets may include greater than 20 sheets. The plurality of sheets may include between 10 and 80 sheets. The plurality of sheets may be made of paper. The plurality of sheets may include polyester. The plurality of sheets may include stone paper. In some embodiments, a first sheet of the plurality of sheets is provided with a cut pattern configured to increase conformability of the first sheet.

DETAILED DESCRIPTION OF ILLUSTRATIVE EMBODIMENTS

Figure 1:
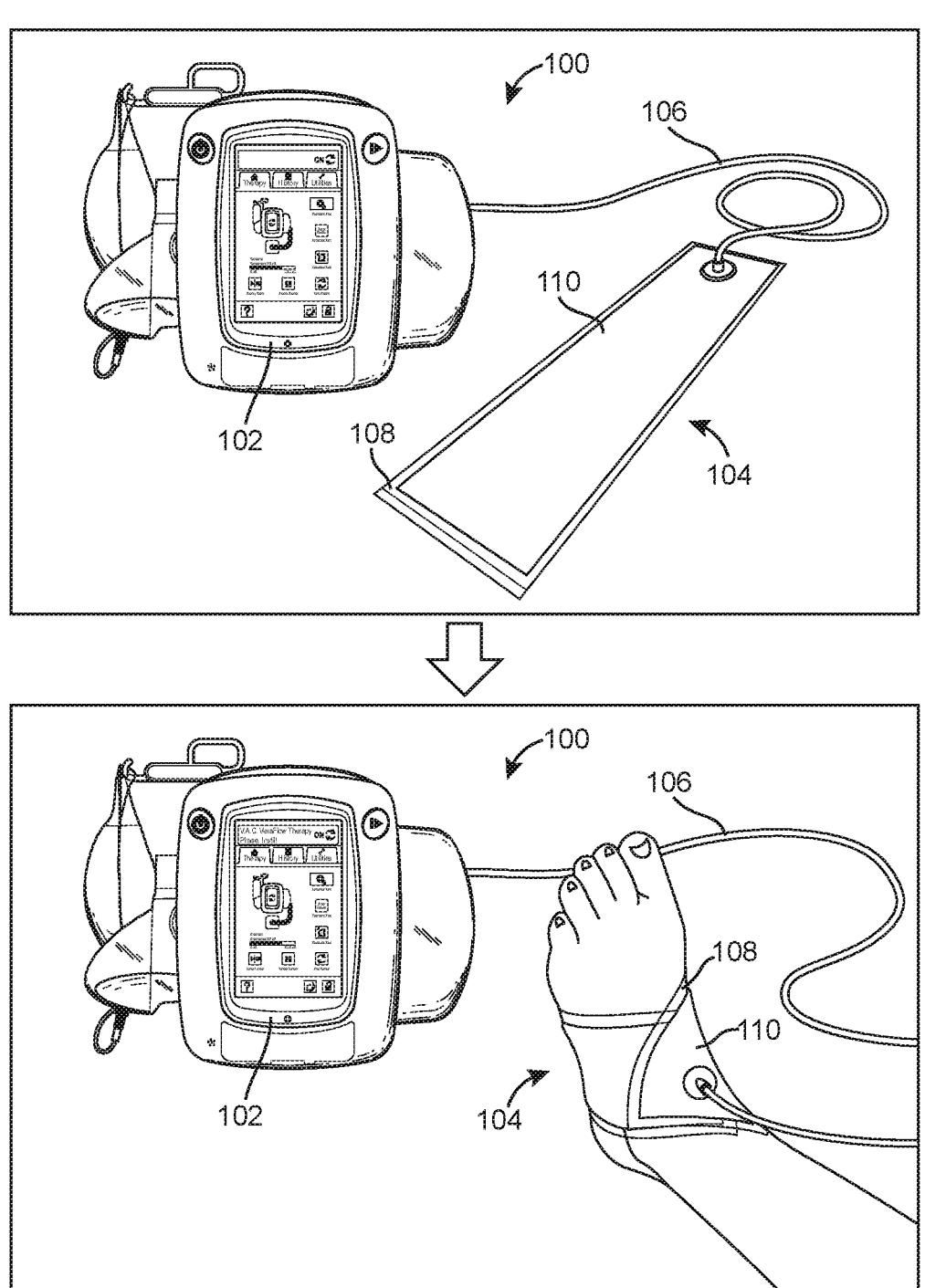
FIG. 1 is storyboard-style illustration of providing immobilization therapy, according to an exemplary embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the FIGURES, an injury treatment system for applying a negative pressure (relative to atmospheric pressure)(e.g., partial vacuum) to intact skin extending over, or surrounding, different types of treatment tissue sites (such as, e.g., bone tissue, adipose tissue, muscle tissue, neural tissue, dermal tissue, vascular tissue, connective tissue, cartilage, tendons, ligaments, etc.) while also immobilizing the tissue site is described according to various embodiments. The application of negative pressure to intact skin provided by the treatment system imparts a pulling (e.g., lifting) force to the intact skin, which decompresses the treatment tissue site and thereby increases the perfusion of blood and other fluids (e.g. lymphatic flow, interstitial fluid) at the treatment tissue site. The decompression of the treatment tissue site resulting from the operation of the treatment system may advantageously reduce swelling at the tissue site. Meanwhile, immobilization can promote healing and prevent aggravation of injuries.

The treatment systems herein may be configured for use in both medical and non-medical settings, and may be used to treat swelling occurring as a result of a variety of different conditions. For example, the treatment system may be used in a home setting by a patient to treat swelling resulting from an injury, over-exertion, an underlying medical condition (e.g., lymphedema), etc. As another example, the treatment system may also be used in a medical setting, such as, e.g., to reduce swelling during pre- and/or post-operative care of a patient. For example, reducing swelling at a treatment site (e.g., caused by a broken bone, edema, tissue sprain, tissue strain, etc.) prior to surgery may advantageously facilitate access to underlying tissue at a target surgical site, reduce surgery time and/or improve the outcome of surgical treatment. Use of a treatment system according to any of the embodiments described herein prior to surgical treatment may advantageously decrease the time needed to reduce swelling at the target surgical site to an acceptable degree of swelling as compared to the time that would be required to reduce swelling using conventional methods of treating swelling. For example, use of the treatment system may reduce swelling to an acceptable degree within 3 to 7 days of initiation of treatment using the treatment system.

In addition to the use of the treatment system to reduce swelling, the decompression therapy provided by the treatment system may advantageously also be used in the treatment of a variety of other medical conditions or ailments. As one non-limiting example, the treatment system may be used for the acute treatment of pain and/or inflammation (occurring, e.g., as a result of a sprain or other stress at a tissue site), for example for treatment of ankles sprains of a variety of severities. In yet other situations, the treatment system may be used to increase blood perfusion and/or lymphatic flow at a treatment tissue site to minimize the effects of over-exertion (e.g., following athletic training or other intense activity). In some embodiments, the treatment system is configured to be reusable, cleanable, and intuitive for a user to self-apply without medical expertise.

Referring now to FIG. 1, a storyboard-style illustration of operation of an injury treatment system 100 is shown, according to an exemplary embodiment. The injury treatment system 100 is shown as including a negative pressure source 102 (e.g., pump), tubing 106, and an immobilization component 104. The immobilization component 104 is coupled to the negative pressure source 102 via the tubing 106. The immobilization component 104 is configured to transform from a flexible state to an inflexible state in response to operation of the negative pressure source 102.

In the example shown, the immobilization component 104 includes an airtight pouch 108. The airtight pouch 108 is substantially airtight, with the exception of a connection to the tubing 106 such that an interior of the airtight pouch is in pneumatic communication with the negative pressure source 102 via the tubing 106. The airtight pouch 108 may be made of a polyurethane drape material.

The immobilization component 104 also includes locking sheets 110 positioned within the airtight pouch 108. When the airtight pouch is at approximately atmospheric pressure, the locking sheets 110 are able to move (e.g., slide) relative to one another within the airtight pouch, which enables the immobilization component 104 to be flexible and conformable. The immobilization component 104 is thus in a flexible state when the airtight pouch is at or above approximately atmospheric pressure (e.g., above a threshold negative pressure). FIG. 1 illustrates that, while in the flexible state, the immobilization component 104 can be wrapped around and/or conformed to an anatomical feature of a patient, for example around a person's foot and ankle as shown in FIG. 1.

Operation of the negative pressure source 102 is configured to reduce the pressure within the airtight pouch 108 of the immobilization component 104, thereby establishing a negative pressure (relative atmospheric pressure) in the immobilization component 104. For example, the negative pressure source 102 may pump air out of the airtight pouch 108 via the tubing 106. The pressure differential between the ambient environment and the interior of the immobilization component 104 causes the locking sheets 110 to be forced towards one another, increasing the friction between the locking sheets 110 and substantially preventing the locking sheets 110 from moving relative to one another. The locking sheets 110 can then be considered as being locked together. When locked together, the locking sheets 110 are inflexible, with each of the locking sheets 110 preventing another of the locking sheets 110 from flexing. The immobilization component 104 is thus in an inflexible state following operation of the negative pressure source 102 to establish a negative pressure at the immobilization component 104.

As shown in FIG. 1, the immobilization component 104 can thus be applied to a patient's anatomy in a desired configuration while in a flexible state, and then transitioned to an inflexible state by operation of the negative pressure source 102. When applied in an appropriate configuration (e.g., a splinting configuration) the immobilization component 104 can substantially immobilize a patient's joint (e.g., ankle, knee, elbow, wrist, shoulder) or other anatomical structure (e.g., foot, hand) while in the inflexible state (i.e., while the immobilization component 104 is maintained at a negative pressure). The immobilization component 104 can thus provide the therapeutic benefits of a splint or cast, while being easy to apply. In some embodiments, the same immobilization component 104 is suitable for application to different joints and/or in various splinting arrangements to provide the medically-preferred immobilization therapy in various possible scenarios.

In some embodiments, release of the negative pressure in the airtight pouch 108 of the immobilization component 104 (e.g., flow of air into the airtight pouch 108) allows the locking sheets 110 to release from one another and returns the immobilization component 104 to the flexible state.

In such embodiments, the immobilization component 104 can be repeatedly switched between the inflexible and flexible states. This can enable reuse of the immobilization component 104 for different injuries or different patients and adjustments of the immobilization therapy over time for a given injury.

Figure 2A:
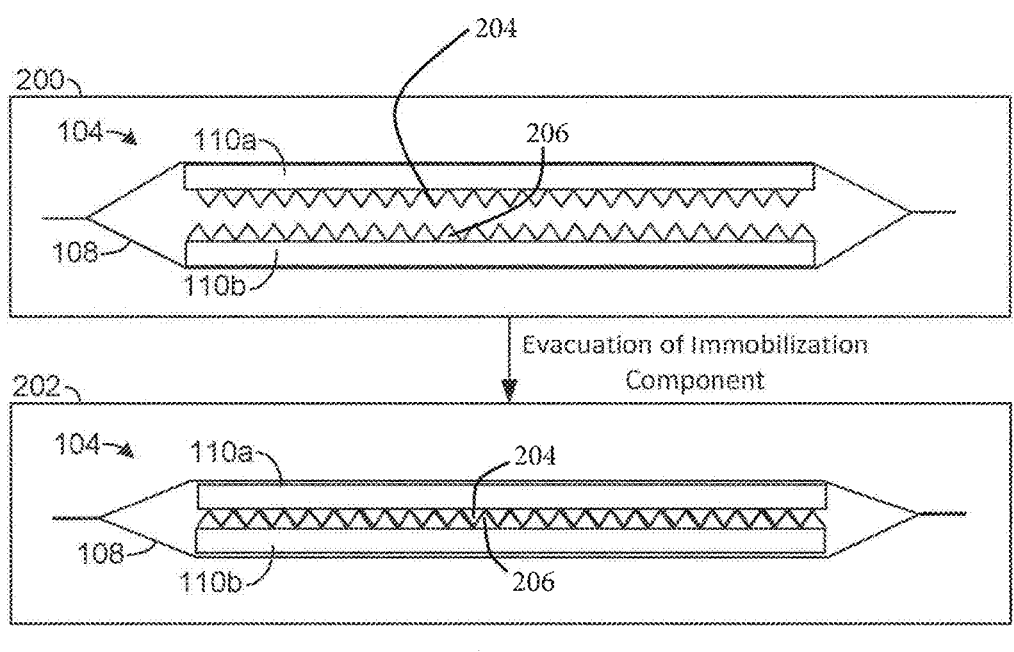
FIG. 2A is a storyboard-style illustration of operation of a first embodiment of locking sheets of an immobilization component of an injury treatment system, according to an exemplary embodiment.

Referring now to FIG. 2A, a close-up cut-away view of one embodiment of the immobilization component 104 transitioning from a flexible state to an inflexible state is shown, according to an exemplary embodiment. In particular, FIG. 2A shows a storyboard-style illustration where the immobilization component 104 is in a flexible state in a first frame 200 and in an inflexible state in a second frame 202, in an example where the immobilization component 104 includes two locking sheets 110.

As shown in the first frame 200, the immobilization component 104 includes locking sheets 110 (shown as a first locking sheet 110a and a second locking sheet 110b) positioned in the airtight pouch 108, with the airtight pouch 108 at substantially atmospheric pressure. When the airtight pouch 108 is at substantially atmospheric pressure, space is provided between the first locking sheet 110a and the second locking sheet 110b which allows for movement of the first locking sheet 110a relative to the second locking sheet 110b, including both horizontally and vertically from the perspective of FIG. 1. The first locking sheet 110a and the second locking sheet 110b are individually flexible, such that when arranged as shown in the first frame 200, the locking sheets 110 allow the immobilization component 104 to be flexed, for example bent into a desired splinting configuration.

When the airtight pouch 108 is evacuated (e.g., brought to a negative pressure by operation of the negative pressure source 102), the immobilization component 104 transitions to the inflexible state shown in the second frame 202. Due to the pressure differential between the interior of the airtight pouch 108 and the exterior of the airtight pouch 108, the airtight pouch 108 is compressed and the locking sheets 110 are forced together. Thus as shown in FIG. 1, the first locking sheet 110a is brought into contact with the second locking sheet 110b and forced against the second locking sheet 110b. The pressure differential can thereby create a high amount of friction between the first locking sheet 110a and the second locking sheet 110b, while preventing movement of the first locking sheet 110a away from the second locking sheet 110b.

Surface texture or elements of the locking sheets 110 can help to lock the locking sheets 110 in position relative to each other. In the example of FIG. 2A, the first locking sheet 110a is provided with first protrusions 204 and the second locking sheet is provided with second protrusions 206. In the example shown, when the immobilization component is transitioned to the inflexible state the first protrusions 204 are moved into recesses between the second protrusions of the second locking sheet 110b, while the second protrusions 206 are moved into recesses between the first protrusions 204 of the first locking sheet 110a. The first protrusions 204 thereby interface with the second protrusions 206 such that the first locking sheet 110a is prevented from sliding along the second locking sheet 110b.

FIG. 2A shows an example including two locking sheets 110. In other embodiments, three or more (e.g., four, five, six, seven, eight, nine, etc.) locking sheets 110 are included. The locking sheets 110 can be made of paper (e.g., a wood-pulp based material), other organic material, a polyethylene material, a polymer, or some combination thereof. In some examples, the locking sheets 110 are configured as described in U.S. Pat. No. 10,538,049, granted 21 Jan. 2020, the entire disclosure of which is incorporated by reference herein.

Figure 2B:
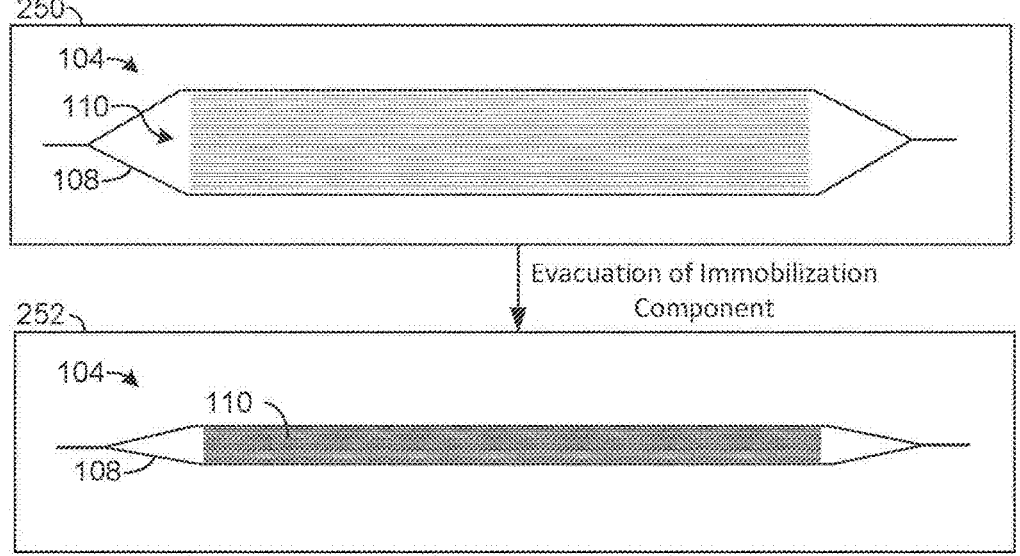
FIG. 2B is a storyboard-style illustration of operation of a second embodiment of locking sheets of an immobilization component of an injury treatment system, according to an exemplary embodiment.

Referring now to FIG. 2B. FIG. 2B shows an example embodiment where a large number of locking sheets 110 are included in the immobilization component 104. In the example of FIG. 2B, the locking sheets 110 are thin and substantially flat (e.g., without the protrusions of FIG. 2A). The number of locking sheets 110 may be in a range between 10 and 80 sheets, for example between 20-40 sheets or greater than 20 sheets (e.g., 25, 50, 100, 200, etc.). As shown in FIG. 2B, thirty locking sheets 110 are included. Each sheet may have a thickness in a range between approximately 0.002" and 0.010", for example between approximately 0.004" and 0.006". When combined, the large number of locking sheets 110 may combine to provide a thickness of less than 0.25", for example a combined thickness between 0.125" and 0.25".

The locking sheets 110 can be made of paper, for example 30 lb paper. Paper provides conformability and flexibility of each locking sheet 110, while also providing for a sufficient amount of friction between the sheets (e.g., due to the fiber structure of paper) and inflexibility of the combined sheets when the immobilization component is in the pressurized, inflexible state. The locking sheets 110 can also be made of polyester, for example polyethylene terephthalate, other plastics, or a paper-like material made of calcium carbonate (or other minerals) with binders (known as stone paper). Such materials are waterproof and can be used in applications where moisture may reach the locking sheets 110.

In the example of FIG. 2B, when the airtight pouch 108 is at substantially atmospheric pressure (as shown in the first frame 250), the large number of locking sheets 110 are free to move and flex relative to each other. Each locking sheet 110 is flexible and conformable, such that, at substantially atmospheric pressure, the immobilization component 104 is flexible and conformable.

When air is evacuated from the airtight pouch 108 and the airtight pouch 108 is brought to at least threshold negative pressure (as shown in the second frame 252), the large number of locking sheets 110 are jammed together by the pressure differential between the interior and exterior of the airtight pouch 108. The surface friction between the sheets 110 is sufficient to create a locked condition, where the sheets 110 are substantially unable to move relative to one another. For example, in examples where the sheets 110 are made of paper, the fibers of neighboring sheets 110 interact to provide a desirable coefficient of friction between the sheets 110. The locking sheets 110 thus form as a substantially solid block made up of the locking sheets 110 and which is inflexible and non-conformable, for example with a combined thickness between of less than approximately 0.25", for example a combined thickness between approximately 0.125" and 0.25". The locking sheets 110 thus lock together to rigidify the immobilization component 104.

Figure 3:
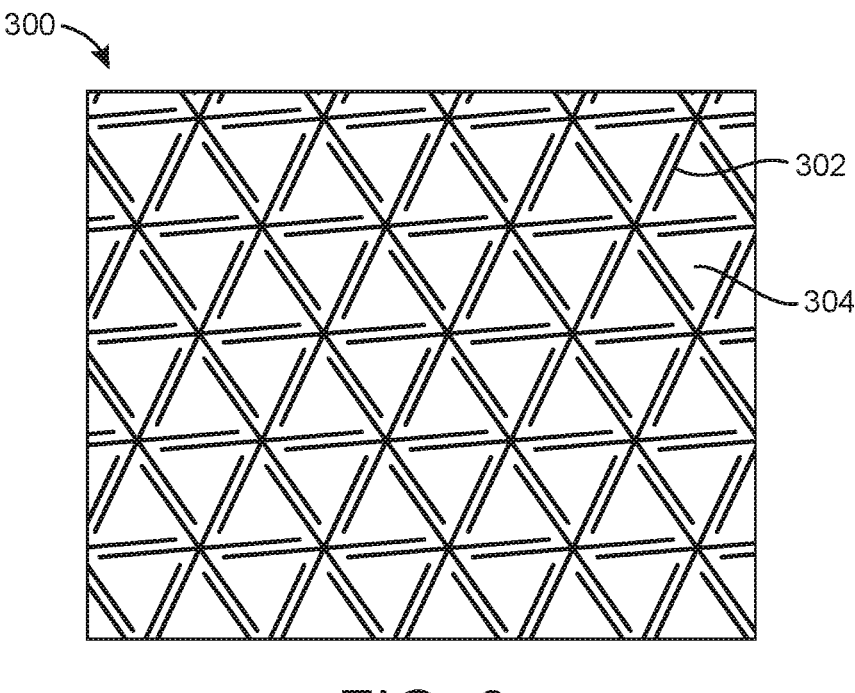
FIG. 3 is a view of an example embodiment of a locking sheet of an immobilization component of an injury treatment system, according to an exemplary embodiment.

FIG. 3 shows a top view of a locking sheet 300, according to an example embodiment. The locking sheet 300 can be an example of one of the locking sheets 110 of FIGS. 1-2B in an example embodiment. As shown in FIG. 3, the locking sheet 300 is textured or cut through to have a patterned surface which provides for both increased flexibility of the locking sheet 300 when the immobilization component 104 is in the flexible state. For example, the locking sheet 300 can be provided with a pattern that is cut into the locking sheet 300 with a rotary die.

In the example shown, the locking sheet 300 includes triangular pattern formed by alternating recesses (cuts, channels, etc.) and non-recessed areas, non-cut areas, etc. on the surface of the locking sheet 300. The recesses may provide areas of increased flexibility for the locking sheet 300. The recesses may be depressions in the locking sheet 300, or may extend all the way through the locking sheet 300. As shown in FIG. 3, the triangular pattern provides numerous linear recesses (e.g., recess 302) which intersect and combine to extend across the locking sheet 300 in three directions to form a large number of triangular shapes (e.g., triangle 304) at the locking sheet 300, thereby providing the locking sheet 300 with a high degree of flexibility and conformability. Other geometries (e.g., pentagonal, hexagonal, etc.) may be used in various embodiments. The interior of the triangular shapes (e.g., triangle 304) can be textured, for example provided with a rough finish or with alternating protrusions and recesses. The locking sheet 300 may thereby configured to provide a high amount of friction when pressed against another instance of the locking sheet 300. In examples where a the locking sheet 300 includes a pattern of recesses (cuts, channels, etc.) as in FIG. 3, a larger number of locking sheets may be used (e.g., greater than 30 sheets, between 30 and 50 sheets) to achieve sufficient inflexibility in the inflexible state.

Figure 4:
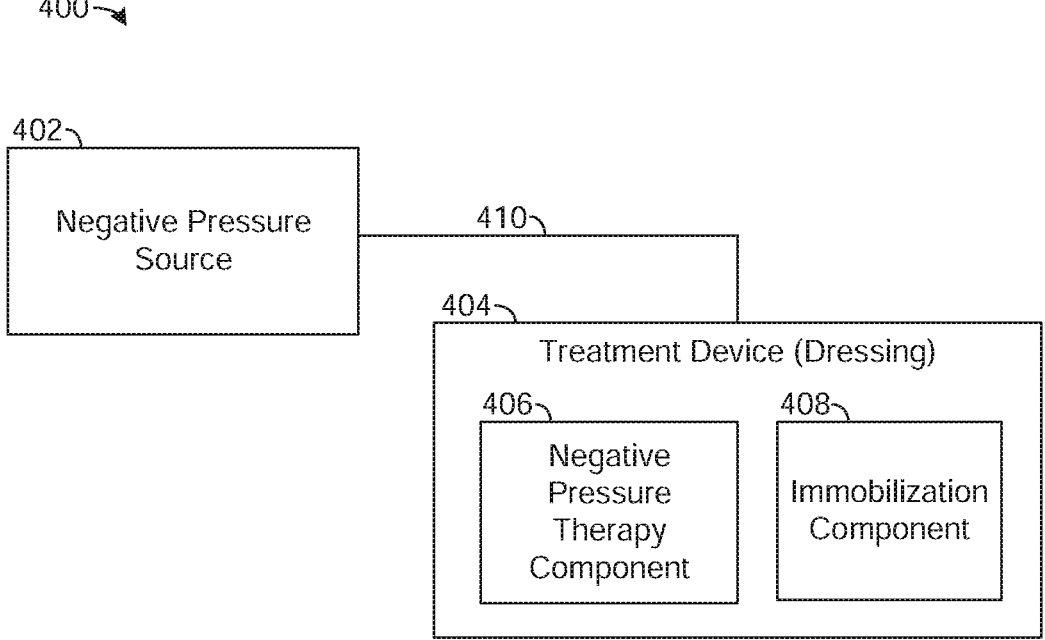
FIG. 4 is a block diagram of an injury treatment system, according to an exemplary embodiment.

Referring now to FIG. 4, a block diagram of an injury treatment system 400 is shown, according to an exemplary embodiment. The injury treatment system 400 is configured to provide integrated negative pressure therapy and immobilization therapy to an injury site, for example a patient's joint. As described below, the injury treatment system 400 advantageously enables negative pressure therapy and immobilization therapy via a shared source of negative pressure. In FIG. 4, the injury treatment system 400 is shown as including a negative pressure source 402 in pneumatic communication with a treatment device (dressing, therapy device, etc.) 404 (which includes a negative pressure therapy component 406 and an immobilization component 408) via tubing 410.

The negative pressure source 402 is configured to supply a negative pressure for the treatment device 404, for example by pumping air out of the treatment device and into an ambient environment. For example, the negative pressure source 402 can include a pump. In some embodiments, the negative pressure source 402 includes a manually-operated pump. In other embodiments, the negative pressure source 402 includes an electrically-powered pump. In some such embodiments, the negative pressure source 402 includes one or more batteries (e.g., rechargeable batteries) that provide electrical power to the electrically-powered pump. In various embodiments, the negative pressure source 402 can include sensors for determining a pressure at the treatment device 404 and controller circuitry for controlling the provision of negative pressure to the treatment device.

The treatment device 404 is shown as including the negative pressure therapy component 406 and the immobilization component 408. In the embodiment shown, the negative pressure therapy component 406 and the immobilization component 408 are integrated together (e.g., unified, combined, fabricated together, etc.) to from the treatment device 404. In other embodiments, the negative pressure therapy component 406 and the immobilization component 408 can be provided separately (e.g., see FIG. 1). The treatment device 404 is configured to be easily applied to a tissue site (e.g., joint) while pressure in the treatment device 404 is at approximately atmospheric pressure and to be sealed over the tissue site. The negative pressure source 402 can then be operated to create and maintain a negative pressure at the treatment device, for example at or beyond a threshold negative pressure. When the negative pressure is established, the treatment device 404 provides both negative pressure therapy to the tissue site (via the negative pressure therapy component 406) and immobilization of the tissue site (via the immobilization component 408).

Figure 8:
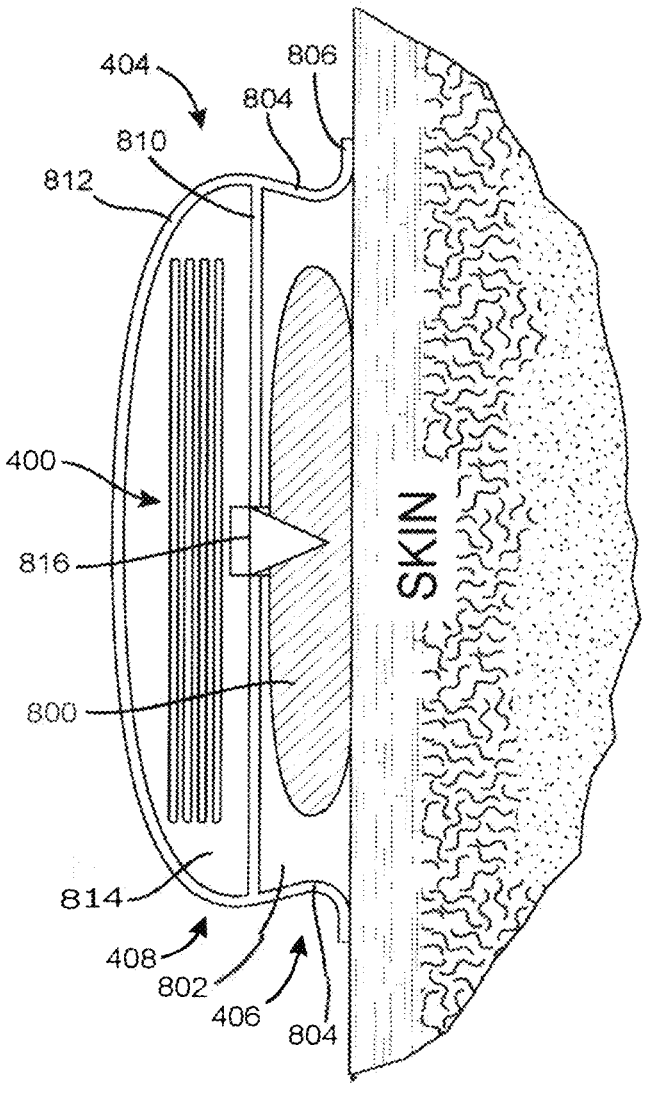
FIG. 8 is a cut-away view of a dressing of the injury treatment system, according to an exemplary embodiment.

The negative pressure therapy component 406 can include a decompression layer (e.g., manifolding layer) and a drape layer, for example as shown in FIG. 8 and described in detail therein. The drape layer is sealable to over the tissue site to established a substantially-airtight volume over the tissue site which encloses the decompression layer. An adhesive (e.g., silicone adhesive), thermoplastic elastomer sealing ring, zipper, strap, or other attachment and seal device can be included to seal the negative pressure therapy over a tissue site.

The decompression layer is configured to allow airflow through and communication of pressure throughout a substantially air-tight defined between the drape layer and a tissue site (when the negative pressure therapy component 406 is sealed over the tissue site). In some embodiments, the decompression layer is made of an open-celled foam, which may be configured to compress when the negative pressure is established at the negative pressure therapy component 406. In other embodiments, the decompression layer includes a macro-mesh or other collapsible layer. For example, the decompression layer can be structured with a stiffer outer portion and a softer (more compressible/collapsible) inner portion, such that the decompression layer tends to collapse in a direction away from the tissue site. In some examples, the negative pressure therapy component 406 is configured as described in U.S. Provisional Patent Application No. 63/133,882, filed 5 Jan. 2021, the entire disclosure of which is incorporated by reference herein.

When negative pressure is established at the negative pressure therapy component 406 of the treatment device 404, the negative pressure imparts a pulling (e.g., lifting) force to the intact skin, which decompresses the treatment tissue site and thereby increases the perfusion of blood and other fluids (e.g. lymphatic flow, interstitial fluid) at the treatment tissue site. Evidence suggests that this pulling or lifting force can encourage swelling reduction, for example significantly reducing the amount of time required for a given amount of swelling to dissipate as compared to not providing negative pressure therapy. In some cases, swelling reduction via decompression therapy as provided by the negative pressure therapy component 406 outperforms conventional swelling management provide using compression wraps or compressive therapy.

One aspect of the present disclosure is that decompression therapy can be enhanced by or complemented by simultaneous immobilization of the tissue site. For example, immobilization of bones of a joint relative to one another (e.g., of a femur relative to a tibia, of a tibia or fibula relative to bones of the foot, etc.), referred to herein as immobilization of the joint, can protect the soft tissue of the joint from further injury or re-injury during the swelling-reduction process. Immobilization therapy provides continued protection for the joint as the patient's natural swelling response is reduced using negative pressure therapy. Thus, it is advantageous to provide integrated and coordinated immobilization and negative pressure treatment.

Figure 5:
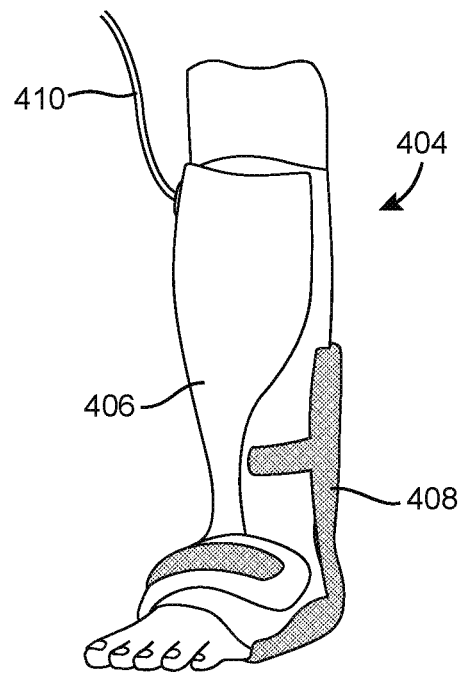
FIG. 5 is a perspective view of an embodiment of a dressing of the injury treatment system of FIG. 4, according to an exemplary embodiment.
Figures 6, 7:
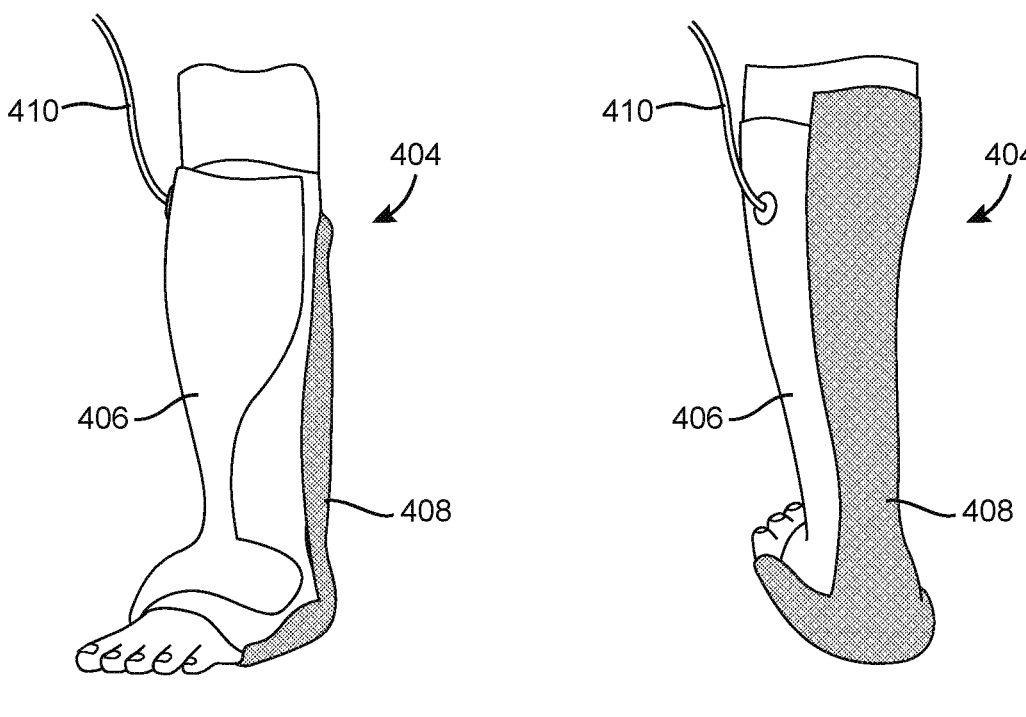
FIG. 6 is a perspective view of another embodiment of a dressing of the injury treatment system of FIG. 4, according to an exemplary embodiment.
FIG. 7 is another perspective view of the dressing of FIG. 4, according to an exemplary embodiment.

Accordingly, the treatment device 404 includes the immobilization component 408. The immobilization component 408 can be configured substantially as described above for the immobilization component 104 of FIGS. 1-3. In the example of FIG. 4, the immobilization component 408 is an integral part of the treatment device 404 and is coupled to and/or formed with the negative pressure therapy component 406. For example, the immobilization component 408 can be positioned at an exterior of the drape layer of the negative pressure therapy component 406, as shown in FIGS. 5-8. In some embodiments, the immobilization component 408 is substantially coextensive with the negative pressure therapy component 406, thereby covering substantially the same extent of a tissue site as the negative pressure therapy component 406. In other embodiments, for example as shown in FIGS. 5-7 and described in detail with reference thereto, the immobilization component 408 is less-than-coextensive with the negative pressure therapy component 406 and is selectively provided in a preferred splinting arrangement to provide a desired immobilization to a joint.

Referring now to FIG. 5, a first example embodiment of the treatment device 404 applied to an ankle of a patient is shown, according to an example embodiment. In the example shown, the treatment device 404 is designed particularly for treatment of an ankle injury or injury to an anatomical feature near the ankle, for example a sprained ankle or broken ankle. As shown, the negative pressure therapy component 406 is provided with a boot- or sock-like shape (e.g., with an open region) so as to fit over the patient's foot, ankle, and lower leg. The negative pressure therapy component 406 may be formed with an annular structure, or, as shown in FIG. 5, may be folded or wrapped around the ankle to achieve the boot-like shape shown in FIG. 5. The negative pressure therapy component 406 provides substantially full-coverage of the affected anatomical region, thereby providing decompression therapy at the ankle and surrounding tissues.

In FIG. 5, the immobilization component 408 is positioned selectively only a portion of the negative pressure therapy component 406. In the example of FIG. 5, the immobilization component 408 extends across a top of the foot region, under the foot, around the heel, and up along the Achilles region to a mid-calf position. The immobilization component 408 also includes a tab extending from the lower calf around towards the shin. The immobilization component 408 is thereby positioned to restrict movement of the ankle joint in various directions, without being overly cumbersome or uncomfortable for the patient.

FIGS. 6-7 show another example embodiment of the treatment device 404 as applied to an ankle of a patient. In FIGS. 6-7, the immobilization component 408 is provided in a splinting arrangement where the immobilization component 408 extends along a bottom of the patient's foot, around the heel, and to an upper-calf position. When activated, the immobilization component 408 thus prevents the patient from flexing their foot downward (e.g., beyond 90 degrees), but may allow some upward movement. Various splinting arrangements for the immobilization component 408 are possible to provide clinically-appropriate joint immobilization to promote healing and/or swelling reduction.

In some cases, the presence of the immobilization component 408 in a given position can enhance the ability of the negative pressure therapy component 406 to exert a pulling force on the tissue at that position. For example, when the immobilization component 408 is rigid, the immobilization component 408 can provide an opposition to the reactive force of the tissue pulling back on the decompression layer. The immobilization component 408 may therefor also be placed in positions where additional/targeted decompression of the tissue site is desired.

Figures 9, 10:
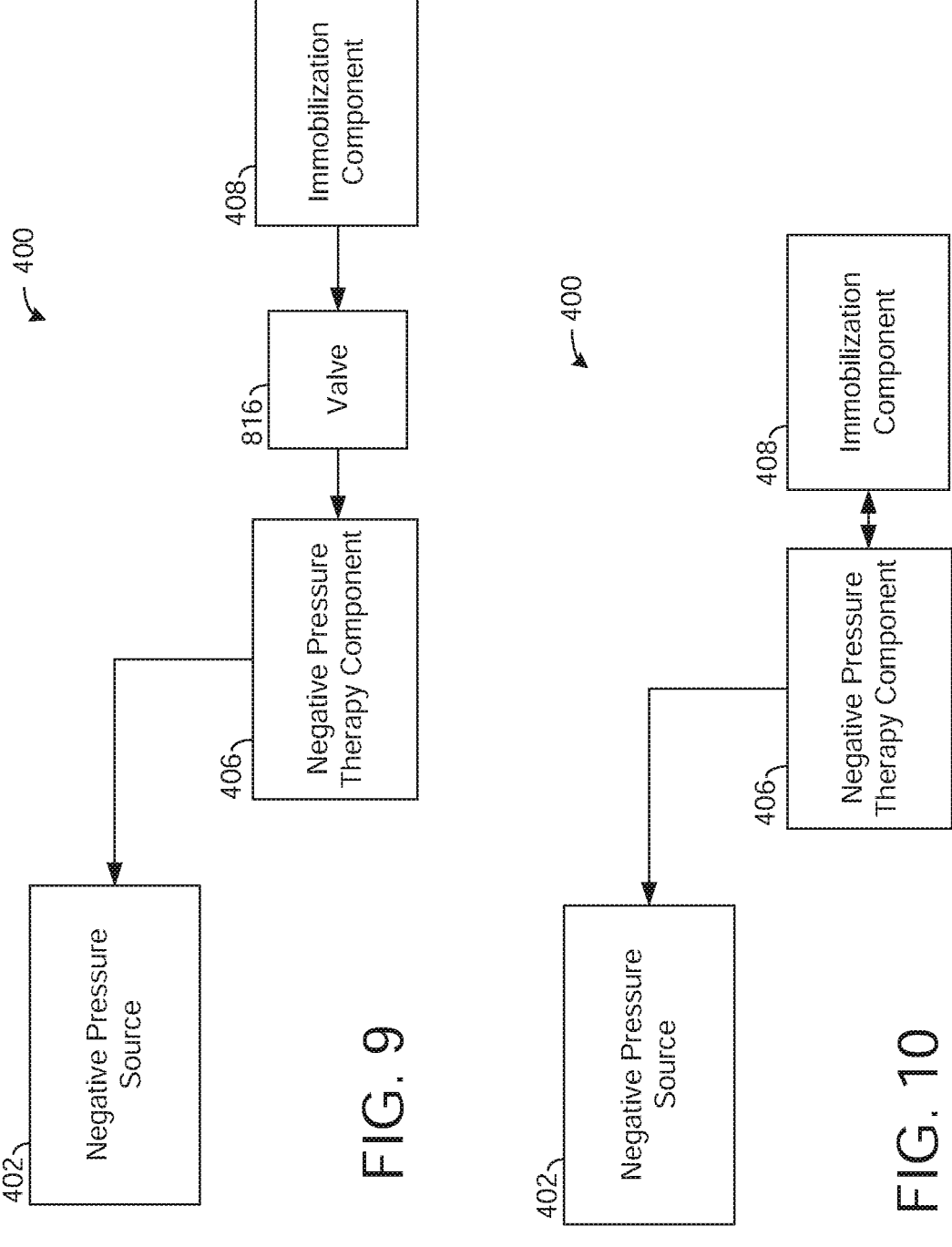
FIG. 9 is a block diagram of the injury treatment showing a first example airflow pathway, according to an exemplary embodiment.
FIG. 10 is a block diagram of the injury treatment showing a second example airflow pathway, according to an exemplary embodiment.
Figures 11, 12:
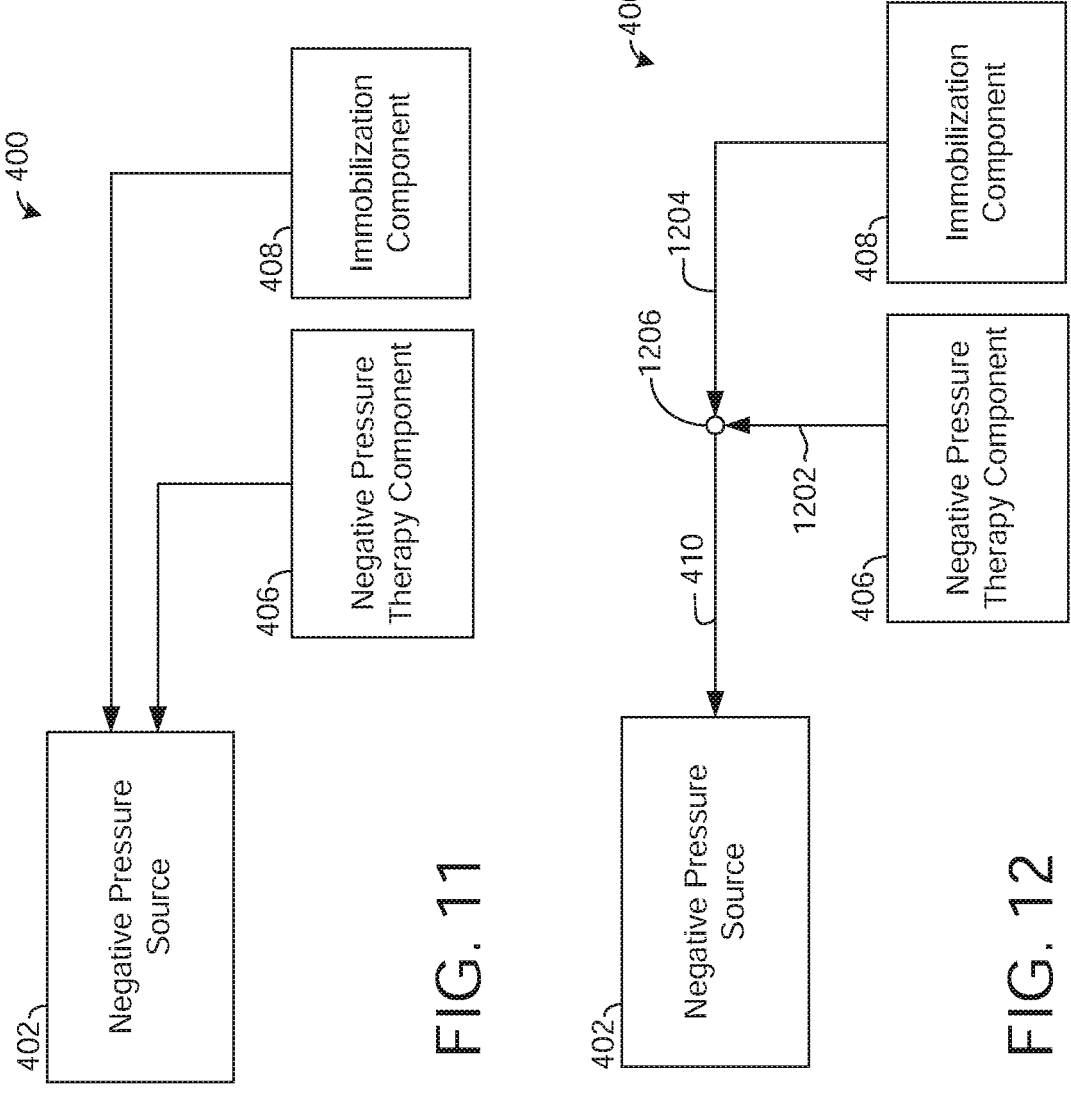
FIG. 11 is a block diagram of the injury treatment showing a third example airflow pathway, according to an exemplary embodiment.
FIG. 12 is a block diagram of the injury treatment showing a fourth example airflow pathway, according to an exemplary embodiment.

In FIGS. 5-7, the tubing 410 is shown as extending only to the negative pressure therapy component 406, such that FIGS. 5-7 show examples where the immobilization component 408 is pneumatically communicable with the tubing 410 and the negative pressure source 402 via the negative pressure therapy component 406. Such embodiments are shown in FIGS. 8-10 as explained below. In other embodiments, as shown in FIGS. 11-12 and explained below, separate tubing extends directly to both the negative pressure therapy component 406 and the immobilization component 408.

FIG. 5-7 also show examples where the immobilization component 408 is contiguous. In other examples, multiple, non-contiguous sections of the immobilization component 408 may be provided on the negative pressure therapy component 406 to achieve desired therapeutic effects.

Referring now to FIG. 8, a close-up cut-away view of an example embodiment of the treatment device 404 applied over intact skin at a tissue site is shown, according to an example embodiment. The negative pressure therapy component 406 abuts the intact skin and is positioned between the skin and the immobilization component 408.

The negative pressure therapy component 406 is shown as including a decompression (manifolding) layer, shown as foam 800. The foam 800 is an open-celled foam which allows airflow therethrough, such that an air pressure is substantially uniform throughout the foam 800. The foam 800 is positioned in a substantially airtight volume 802 defined by the intact skin and a drape layer 804 of the negative pressure therapy component 406. The drape layer 804 is sealed to the skin at a border 806 of the drape layer 804, for example with an adhesive, elastomer ring, or some other seal. In some cases, for example variations of the examples of FIGS. 5-7, the drape layer 804, the foam 800, and the substantially airtight volume 802 are formed in an annular structure such that a seal can be provided just at open ends of the annular structure.

A middle portion 810 of the drape 804 defines both the substantially airtight volume 802 for the negative pressure therapy component 406 and is a part of a substantially airtight pouch 812 of the immobilization component 408. Thus, an interior volume 814 of the airtight pouch 812 of the immobilization component 408 is separated from the airtight volume 802 of the negative pressure therapy component 406 by the middle portion 810 of the drape 804.

The drape 804 and the airtight pouch 812 can formed of the same material to facilitate manufacturing, for example to facilitate heat fusion or ultrasonic welding of the drape 804 and the airtight pouch 812. For example, the drape 804 and the airtight pouch 812 can be formed of a non-permeated polyurethane material configured to be flexible but non-stretchable under the range of forces experienced by the treatment device 404 in normal use.

As shown in FIG. 8, the immobilization component 408 includes locking sheets 110 positioned in the airtight pouch 812. In the example shown, four locking sheets 110 are provided. The locking sheets are positioned to be substantially parallel to the intact skin over which the treatment device 404 is applied, and substantially parallel to the middle portion 810 of the drape 804 which defines the border between the negative pressure therapy component 406 and the immobilization component 408.

In FIG. 8, the treatment device 404 is also shown as including a one-way valve 816 (e.g., one-way baffle) positioned on the middle portion 810 of the drape 804 such that the valve 816 is communicable with both the interior volume 814 of the airtight pouch 812 of the immobilization component 408 and with the airtight volume 802 of the negative pressure therapy component 406. The one-way valve 816 is configured to allow air to flow out of the airtight pouch 812, across the middle portion 810 of the drape 804, and into the airtight volume 802, while preventing airflow in the opposite direction. The airflow may be caused by operation of the negative pressure source 402 connected to the airtight volume 802 of the negative pressure therapy component 406 via tubing 410. Thus, in the embodiment of FIG. 8, the negative pressure source 402 operates to draw a negative pressure in the airtight pouch 812 of the immobilization component 408 by causing air to be drawn through the valve 816 and to the tubing 410 via the negative pressure therapy component 406, for example via the foam 800 or other manifolding or decompression layer.

Movement of air out of the airtight pouch 812 causes the immobilization component 408 to transition from a flexible state to an inflexible state, as described above with reference to FIG. 1-3. In particular, when the airtight pouch 812 reaches at least a threshold negative pressure, the locking sheets 110 are forced together into a rigid and immobile state. By preventing airflow back into the airtight pouch 812, the one-way valve 816 causes the immobilization component 408 to stay in the inflexible state, regardless of pressure fluctuations at the negative pressure therapy component 406. This can advantageously protect a joint or other tissue site by maintaining immobilization of the joint even if pressure is lost elsewhere in the injury treatment system.

In some embodiments, the valve 816 is configured to permanently seal in response to pressure in the airtight pouch 812 of the immobilization component 408 reaching a threshold amount of negative pressure, for example a value in a range between approximately −75 mmHg and approximately −150 mmHg (e.g., −125 mmHg). In such embodiments, the treatment device 404 may be a single-use device. In other embodiments, the one-way valve 816 can be selectively opened by a user the user to allow air to flow back into the airtight pouch 812, thereby allowing the immobilization component to transition back to the flexible state. In other embodiments, a separate user-selectable valve is provided on the airtight pouch 812 to allow a user to selective release the negative pressure to transition to the flexible state. Such embodiments may enable easy removal of the treatment device 404 from a patient and reuse of the treatment device 404.

Referring now to FIGS. 9-12, a variety of embodiments of the injury treatment system 400 having different airflow pathways are shown, according to exemplary embodiments. In particular, the schematic drawings of FIGS. 9-12 show the elements of the injury treatment system 400 (i.e., the negative pressure source 402, the negative pressure therapy component 406, and the immobilization component 408) connected together via tubing 110 in a variety of ways which provide different airflow pathways through the elements of the injury treatment system 400. Thus, various airflow pathways that enable the treatment device 404 to be drawn down to at a negative pressure in different embodiments are shown.

For example. FIG. 9 schematically illustrates an airflow pathway consistent with the embodiment of FIG. 8. As shown in FIG. 9, air flows out of the immobilization component 408, across the valve 816, and through the negative pressure therapy component 406 to the negative pressure source 402. The elements are connected in series along the airflow pathway.

As the next example, FIG. 10 schematically illustrates a variation of the embodiment of FIGS. 8-9 where the valve 816 has been omitted. In such embodiments, air may flow freely between the negative pressure therapy component and the immobilization component 408. For example, with reference to FIG. 8, the middle portion 810 of the drape 804 may be omitted or perforated to allow pressure to be communicated in either direction between the negative pressure therapy component 406 and the immobilization component 408.

As another example, FIG. 11 schematically illustrates an embodiment of the injury treatment system 400 where the negative pressure therapy component 406 and the immobilization component 408 are independently connected to the negative pressure source 402 (i.e., in parallel). In some such embodiments, the negative pressure source 402 operates to simultaneously draw air out of both the negative pressure therapy component 406 and the immobilization component 408. In other versions of the embodiment of FIG. 11, the negative pressure source 402 is operable to independently and selectively draw air out of either the negative pressure therapy component 406 or the immobilization component 408, but not necessarily both simultaneously. In some such embodiments, the negative pressure source 402 includes two independent pumps.

As yet another example, FIG. 12 shows an embodiment where the tubing 410 extending from the negative pressure source 402 splits into a first section 1202 extending to the negative pressure therapy component 406 and a second section 1204 extending to the immobilization component 408 at a joint 1206. As shown, the joint 1206 is external to both the negative pressure source 402 and the treatment device 404. The joint 12206 is thus accessible and visible to a user of the injury treatment system 400. In some embodiments the joint 1206 includes a valve that can selectively close of the airflow pathway to or from the immobilization component 408. The valve can also be positioned elsewhere along second section 1204 of tubing between the joint 1206 and the immobilization component 408. In such embodiments, the negative pressure source 402 can be operated with the valve open to transition the immobilization component 408 from a flexible state to an inflexible state, and then closed to hold the immobilization component 408 in the inflexible state. To transition back to the flexible state, the valve can be reopened and air can be allowed to flow into the immobilization component 408. The injury treatment system 400 can thus be adapted for repeated adjustments, removal, and reuse.

The examples above including tubing 410. In other examples, the tubing 410 is omitted, for example such that the negative pressure source 402 is mounted directly on the treatment device 404. Many such variations are within the scope of the present disclosure.

Configuration of Exemplary Embodiments

As utilized herein, the terms "approximately." "about." "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary," and variations thereof (e.g., "illustrative"), as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

What is claimed is:

1. An injury treatment system, comprising:
a negative pressure source; and
a dressing pneumatically communicable with the negative pressure source, the dressing comprising:
a negative pressure therapy component configured to expose an anatomical structure to a negative pressure when the negative pressure therapy component is applied to the anatomical structure and in response to operation of the negative pressure source, and an immobilization component coupled to the negative pressure therapy component, wherein the immobilization component is configured to transition from a flexible state to an inflexible state in response to the operation of the negative pressure source.

2. The injury treatment system of claim 1, wherein the negative pressure therapy component comprises a manifolding layer and an air-impermeable layer configured to be sealed to the anatomical structure to define an airtight volume containing the manifolding layer between the air-impermeable layer and the anatomical structure.

3. The injury treatment system of claim 1, wherein the immobilization component is further configured to transition from the inflexible state to the flexible state in response to release of negative pressure from the immobilization component.

4. The injury treatment system of claim 1, wherein the immobilization component is pneumatically communicable with the negative pressure source via the negative pressure therapy component.

5. The injury treatment system of claim 4, wherein the immobilization component is pneumatically communicable with the negative pressure source via a valve configured to close when a threshold amount of negative pressure is established in the immobilization component.

6. The injury treatment system of claim 1, wherein the immobilization component comprises:

an air-tight chamber configured to be evacuated by the operation of the negative pressure source; and locking sheets positioned in the airtight chamber, wherein:

the locking sheets are flexible when the airtight chamber is not evacuated, and the locking sheets interlock to form a rigid structure when the air-tight chamber is evacuated by the operation of the negative pressure source.

7. An injury treatment device, comprising:

a manifold layer having a patient-facing side and a non-patient-facing side;

a first airtight chamber positioned along at least a portion of the non-patient-facing side of the manifold layer;

locking sheets positioned in the first airtight chamber, the locking sheets configured to transition from a flexible state to an inflexible state;

a sealable layer coupled to the manifold layer and configured to be sealed to a patient to define a second airtight chamber that contains the manifold layer; and a valve configured to selectively place the first airtight chamber in fluid communication with the second airtight chamber.

8. The injury treatment device of claim 7, wherein:

when the first airtight chamber is at atmospheric pressure, the locking sheets are flexible; and when the first airtight chamber is drawn to at least a threshold negative pressure, the locking sheets are inflexible.

9. The injury treatment device of claim 8, wherein the threshold negative pressure is −125 mmHg.

10. The injury treatment device of claim 7, wherein the locking sheets comprise:

a first sheet having protrusions arranged in a first pattern;

a second sheet having recesses arranged in the first pattern;

wherein the first sheet is substantially prevented from sliding along the second sheet when the protrusions are positioned in the recesses, thereby rendering the locking sheets inflexible.

11. The injury treatment device of claim 10, wherein the protrusions are configured to enter the recesses in response to establishment of a negative pressure in the first airtight chamber and move out of the recesses in response to release of the negative pressure from the first airtight chamber.

12. The injury treatment device of claim 7, wherein the injury treatment device is configured for application to an ankle, and:

the locking sheets are less-than-coextensive with the manifold layer.

13. The injury treatment device of claim 12, wherein the locking sheets are provided in a splinting arrangement configured to substantially immobilize the ankle when the locking sheets are in the inflexible state and to allow the ankle to be inserted into the manifold layer when the locking sheets are in the flexible state.

14. A method of treating an injury to a joint, comprising:

applying a treatment device around the joint;

sealing one or more edges of the treatment device to the joint to define a first airtight chamber containing a manifold layer;

providing negative pressure therapy by pumping air out of the first airtight chamber to communicate a negative pressure to the joint; and providing immobilization therapy by pumping air out of a second airtight chamber, the second airtight chamber containing locking sheets configured to immobilize the joint in response to the second airtight chamber reaching at least a threshold negative pressure.

* * * * *